(12) United States Patent
Wong et al.

(10) Patent No.: US 11,110,205 B2
(45) Date of Patent: Sep. 7, 2021

(54) FORMULA FOR SYNTHESIZING BONE REPLACEMENT MATERIAL, AND MANUFACTURING METHOD AND APPLICATION METHOD THEREOF

(71) Applicant: NOVUS LIFE SCIENCES LIMITED, Hong Kong (CN)

(72) Inventors: Kailun Wong, Hong Kong (CN); Chunglim Wong, Hong Kong (CN); Kingyin Lai, Hong Kong (CN)

(73) Assignee: NOVUS LIFE SCIENCES LIMITED, Hong Kong (CN)

( * ) Notice: Subject to any disclaimer, the term of this patent is extended or adjusted under 35 U.S.C. 154(b) by 0 days.

(21) Appl. No.: 16/319,872

(22) PCT Filed: Jul. 24, 2017

(86) PCT No.: PCT/CN2017/094133
§ 371 (c)(1),
(2) Date: Jan. 23, 2019

(87) PCT Pub. No.: WO2018/019208
PCT Pub. Date: Feb. 1, 2018

(65) Prior Publication Data
US 2019/0240376 A1    Aug. 8, 2019

(30) Foreign Application Priority Data
Jul. 25, 2016 (CN) .......................... 201610590726.4

(51) Int. Cl.
| | | |
|---|---|---|
| A61L 27/12 | (2006.01) | |
| C08F 265/06 | (2006.01) | |
| C08F 220/18 | (2006.01) | |
| A61L 27/48 | (2006.01) | |
| A61L 27/16 | (2006.01) | |
| C08F 220/14 | (2006.01) | |

(52) U.S. Cl.
CPC .............. *A61L 27/48* (2013.01); *A61L 27/12* (2013.01); *A61L 27/16* (2013.01); *C08F 220/14* (2013.01); *A61L 2430/02* (2013.01)

(58) Field of Classification Search
CPC .. C08L 33/12; A61L 2430/02; A61L 2400/06; A61L 2300/606; A61L 2400/240084; A61L 27/46; A61L 31/14; A61L 27/32; A61L 27/12
See application file for complete search history.

(56) References Cited

U.S. PATENT DOCUMENTS

| | | | | |
|---|---|---|---|---|
| 4,268,639 A | * | 5/1981 | Seidel ..................... | A61L 24/06 525/303 |
| 5,085,866 A | * | 2/1992 | Cowsar ................ | A61K 9/0063 424/475 |
| 5,264,215 A | | 11/1993 | Nakabayashi et al. | |
| 8,734,459 B1 | * | 5/2014 | Alobaid ............. | A61B 17/7097 606/92 |
| 8,834,845 B2 | | 9/2014 | Nies et al. | |
| 2012/0271431 A1 | * | 10/2012 | Nies ...................... | A61L 27/042 623/23.53 |
| 2013/0210960 A1 | * | 8/2013 | Lee ...................... | A61L 24/0015 523/116 |
| 2015/0127058 A1 | * | 5/2015 | Beyar ............... | B01F 15/00058 606/86 R |
| 2016/0129148 A1 | | 5/2016 | Wong et al. | |

FOREIGN PATENT DOCUMENTS

| | | |
|---|---|---|
| CN | 87103518 A | 12/1987 |
| CN | 103108660 A | 5/2013 |
| CN | 104093429 A | 10/2014 |
| CN | 105315478 A | 2/2016 |
| WO | WO 2012/018612 A2 | 2/2012 |

OTHER PUBLICATIONS

Gopalarishnanchettiyar et al. Surface-Phosphorylated Copolymer Promotes Direct Bone Bonding. May 25, 2009. Tissue Engineering. vol. 15. No. 10. (Year: 2009).*
Hogt et al. Wettability and Zeta Potentials of a Series of Methacrylate Polymers and Copolymers. Aug. 1985. Journal of Colloid and Interface Science. vol. 106, No. 2. pp. 289-298. (Year: 1985).*
Dalton et al. Manufacture of poly(2-hydroxyethyl methacrylate-co-methyl methacrylate) hydrogel tubes for use as a nerve guidance channels. 2002. Biomaterials. vol. 23. pp. 3843-3851. (Year: 2002).*
Miyazaki, Toshiki, et al., "Bioactive PMMA bone cement prepared by modification with methacryloxypropyltrimethoxysilane and calcium chloride," J. Biomed. Mater. Res. 2003, 67(4) pp. 1417-1423.
Extended European search report dated Feb. 7, 2020 from European patent application No. 17833511.3.
First Chinese Office Action issued in Chinese patent application No. 201610590726.4 dated Feb. 3, 2020.
Sailaja, G. S., et al., "Ultrastructural evaluation of in vitro mineralized calcium phosphate phase on surface phosphorylated poly(hydroxy ethyl methacrylate-co-methyl methacrylate)," J Mater Sci: Mater Med (2010) 21:1183-1193.

(Continued)

*Primary Examiner* — Tracy Liu
(74) *Attorney, Agent, or Firm* — Faegre Drinker Biddle & Reath LLP

(57) ABSTRACT

A bone material composite granule, a manufacturing method and usage method thereof, and a bone cement constructed using the composite granule. The bone material composite granule comprises a co-polymer of a hydroxyethyl methacrylate (HEMA) and methyl methacrylate (MMA) and a calcium phosphate coated on the surface of the co-polymer. A synthesized bone replacement material has improved biocompatibility, bone conduction, and rheological characteristics, and enhanced mechanics and mechanical performance. The bone material can be used in the fields of osteonecrosis, osteoporosis, osteoarthritis, vertebroplasty, bone fracture, bone cyst, alveolar atrophy, subchondral bone defect, subchondral bone cyst, maxillofacial surgery, plastic surgery, minimally invasive procedure, and the like.

14 Claims, 9 Drawing Sheets

(56) References Cited

OTHER PUBLICATIONS

Sailaja, G. S., et al., "Biomimetically Modified Poly (2-Hydroxy Ethyl Methacrylate-Co-Methyl Methacrylate) Microspheres for Bone Augmentation," Trends in Biomaterials and Artificial Organs, Jul. 1, 2006, pp. 3-6.
International Search Report and Written Opinion dated Oct. 31, 2017 for PCT/CN2017/094133.

* cited by examiner

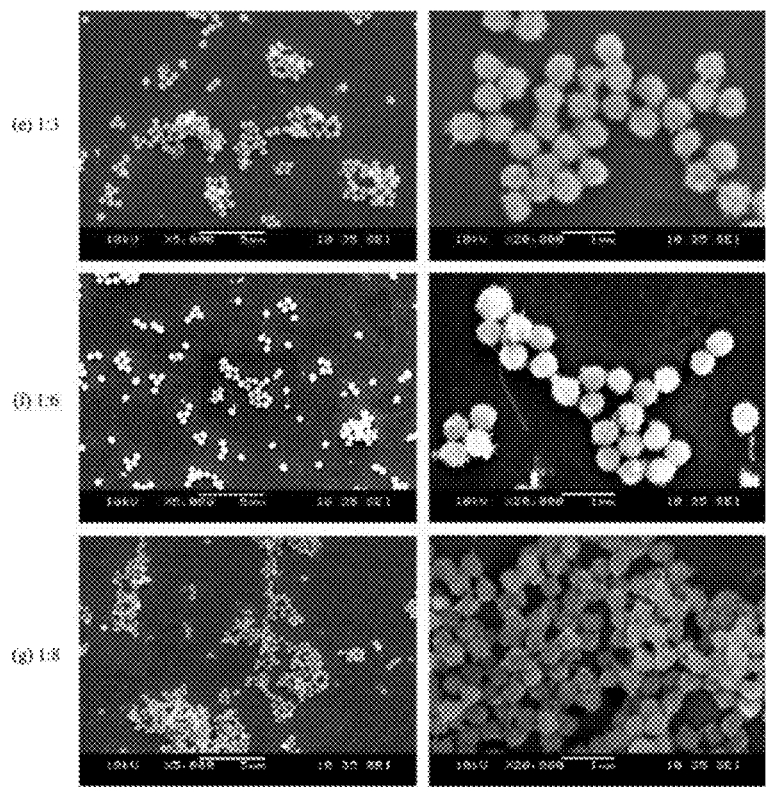
Figure 5
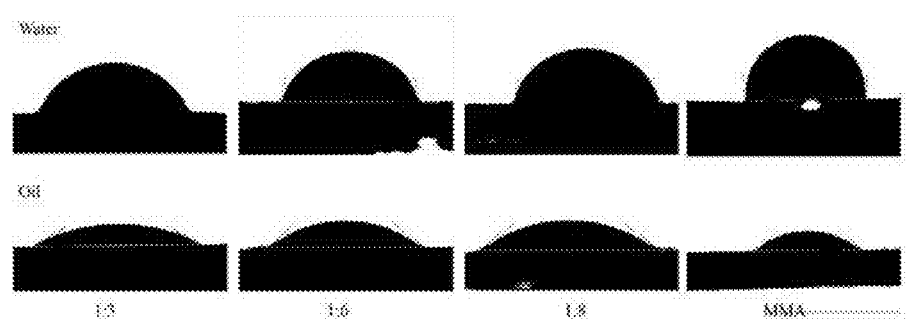
Figure 6
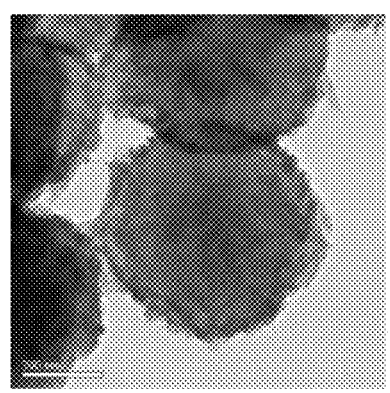

FORMULA FOR SYNTHESIZING BONE REPLACEMENT MATERIAL, AND MANUFACTURING METHOD AND APPLICATION METHOD THEREOF

CROSS REFERENCE TO RELATED APPLICATIONS

This application is a National Stage of International Application No. PCT/CN2017/094133 filed Jul. 24, 2017, which claims benefit of Chinese Patent Application No. 201610590726.4 filed Jul. 25, 2016, both of which are herein incorporated by reference in their entirety.

TECHNICAL FIELD

This invention belongs to the field of bone materials, in particular, the invention relates to the formulation, preparation and application of a new synthetic bone replacement material.

BACKGROUND OF INVENTION

Polymethyl methacrylate (PMMA) bone cement has been widely and clinically used as a bone tissue repair material for many years. Despite it has good physiochemical and mechanical properties, the poor hydrophilic property and its relatively high polymerization temperature lead to poor compatibility between cement material and bone tissue, so that it is difficult to form a good binding to bone tissue. And the high viscosity of bone cement is not conducive to syringe injection. Furthermore, the defects such as the high polymerization temperature of the PMMA (up to 120° C.) insufficient binding of cement to bone, loosening between cement and bone tissues (particularly osteoporotic bone), dislocation and even shedding and the like can easily lead to various postoperative complications. After injecting the current PMMA bone cement, a thin connective tissue is formed on cement surface, which can impair the direct force transfer between the implant and the bone, leading to the premature loosening of the prothesis.

In order to improve the compatibility of the cement and bone, calcium phosphate can be mixed with the cement and can also be coated on the surface of the implant. Miyazaki et al. (J. Biomed. Mater. Res. 2003, 67A(4) 1417-1423) researched the addition of MPS (methacryloxypropyltrimethoxysilane) and calcium chloride to PMMA bone cement to improve bioactivity. The results show that only adding very high concentrations of MPS and calcium chloride to the PMMA bone cement will mineralize the surface. However, the addition of mineralized additives also causes the mechanical properties of the bone cement to significantly deteriorate.

U.S. Pat. No. 52,644,215 B1 discloses the addition of 4-MET monomer (4-methacryloyloxy trimellitic anhydride) or 4-META (4-methacryloyl ethoxy phthalic anhydride) and calcium phosphate, especially hydroxyapatite to bone cement. These bone cement formulations have unreacted monomeric additives that may adversely affect the body.

U.S. Pat. No. 8,834,845 B2 discloses a bio-active bone cement which upon injection, provides a bioactive surface and also promotes the formation of calcium phosphate on the surface of the bone cement.

Calcium phosphate cements (CPCs) have good biocompatibility, bioactivity and osteoconductivity. However, standalone CPCs without any additives have difficulties in injection due to liquid-solid phase separation. Also, the CPCs have weak cohesion and may collapse when coming in contact to blood or biological fluids. Other disadvantages of the CPCs include its poor mechanical properties such as its toughness, brittleness, and reliability, which limit its application.

In conclusion, there is an urgent need in the art to develop new bone materials that have good biocompatibility, good cohesive property, strong plasticity, long durability, and excellent mechanical property.

SUMMARY OF INVENTION

The purpose of the invention is to provide synthesis formula, preparation and application methods of the new bone material.

The first aspect of this invention provides a bone material composite granule comprising a copolymer of hydroxyethyl methacrylate (HEMA) and methyl methacrylate (MMA); and calcium phosphate coated on the surface of the copolymer, wherein, the molar ratio of HEMA to MMA is 1:3-1:15 (preferably 1:4-1:12, more preferably 1:5-1:10).

In another preferred embodiment, the copolymer has an average diameter, $d_1$, in the range of 300-600 nm.

In another preferred embodiment, the average diameter of the bone material composite granule, $d_2$, is 400-900 nm, preferably 500-800 nm and more preferably 550-750 nm.

In another preferred embodiment, $d_2:d_1$ is 1.05-1.2, preferably 1.1-1.8 and more preferably 1.2-1.5.

In another preferred embodiment, the distribution ratio of bone material composite granules between 200-900 nm is ≥95% (preferably ≥96%).

In another preferred embodiment, the bone material composite granules possess one or more of the following properties:

(1) The bending strength of the bone graft made from setting the bone material composite granules is ≥50 MPa (preferably between 50-80 MPa);

(2) The compression strength of the bone graft made from setting the bone material composite granules is ≥100 MPa (preferably between 100-150 MPa);

(3) The setting time of the bone material composite granules is 10-15 mins, preferably 12-15 mins and more preferably 14-15 mins.

The second aspect of the invention provides a fabrication method of the bone material composite granule according to the first aspect of the present invention, comprising the steps of:

(1) Providing a copolymer of hydroxyethylmethacrylate (HEMA) and methyl methacrylate (MMA), wherein, the molar ratio of HEMA to MMA is 1:3-1:15 (preferably between 1:4-1:12, more preferably 1:5-1:10);

(2) Reacting the copolymer with $Ca(OH)_2$ and $H_3PO_4$ to form a copolymer coated with calcium phosphate, thereby preparing the composite granule;

(3) Optionally, drying the composite granule.

In another preferred embodiment, step (1) is conducted between 60-100° C. (preferably 65-95° C., more preferably 70-90° C., and most preferably 75-85° C.).

In another preferred embodiment, step (1) includes step (1-1): HEMA and MMA are mixed and stirred in a potassium persulfate solvent.

In another preferred embodiment, step (1) comprises that HEMA and MMA are mixed and stirred at 80° C. under nitrogen for 3 hours.

In another preferred embodiment, in step (2), the mass ratio of the copolymer to $Ca(OH)_2$ is 1:1-10:1, preferably 2:1-8:1, more preferably 3:1-7:1.

In another preferred embodiment, in step (3), the drying process refers to freeze-drying.

The third aspect of this invention provides a bone cement product which consists of:

(1) Component A, comprising the composite granule according to the first aspect of the invention; and (2) Component B, comprising methyl methacrylate and an accelerator selected from the group consisting of: dimethyl-p-toluidine (DMPT), methyl ethyl ketone peroxide (MEKP), dicumyl peroxide, perester, decanoyl peroxide, t-butane, tert-pentane, azobisisobutyronitrile (AIBN), caproic acid, and combination thereof.

In another preferred embodiment, component A includes a catalyst and a contrast agent.

In another preferred embodiment, the catalyst is selected from the group consisting of: benzoyl peroxide, N,N-dimethylamino-4-benzyl laurate (DMAL), N,N-dimethylamino-4-benzyl oleate (DMAO), and combination thereof.

In another preferred embodiment, the contrast agent is selected from the group consisting of: $BaSO_4$, $ZrO_2$, and combination thereof.

In another preferred embodiment, the mass ratio of the composite granule to the catalyst in component A is 1:1-20:1, preferably 2:1-18:1, more preferably 3:1-16:1, and most preferably 3:1-15:1.

In another preferred embodiment, the mass ratio of the composite granule to the contrast agent in component A is 10:1-80:1, preferably 15:1-70:1, and more preferably 20:1-50:1.

In another preferred embodiment, the volume ratio of methyl methacrylate to the accelerator in component B is 10:1-150:1, preferably 15:1-120:1, and more preferably 30:1-100:1.

In another preferred embodiment, the mass ratio of component A to component B is 1:1-1:20, preferably 1:2-1:15, and more preferably 1:3-1:10.

In another preferred embodiment, component A exists in the solid state and component B exists in liquid phase.

In another preferred embodiment, the static water contact angle of the bone cement product ranges between 67-84°, preferably 70-80°.

In another preferred embodiment, the static oil contact angle of the bone cement product ranges between 29-38°, preferably 32-37°.

The fourth aspect of the invention provides a method for non-therapeutic preparation of a bone graft in vitro, comprising the steps of:

(a) Providing the bone material composite granule according to the first aspect of the present invention;

(b) Mixing the bone material composite granule with a setting liquid to form a mixture; and (c) Setting the mixture to form the bone graft.

In another preferred embodiment, the hardening of the bone graft takes place in a mold.

The fifth aspect of the invention provides use of the composite granule according to the first aspect of the present invention or the bone cement product according to the third aspect of the present invention in the manufacture of a bone filler for treating a bone disease.

In another preferred embodiment, the bone disease is selected from the group consisting of: bone necrosis, osteoporosis, osteoarthritis, vertebroplasty, bone fracture, bone cysts, alveolar bone atrophy, subchondral bone defect, subchondral bone cyst, vertebroplasty, maxillofacial surgery, plastic surgery, and minimal invasive bone surgery.

It is to be understood that within the scope of this invention, each technical feature of the invention mentioned above and each technical features specifically described hereinafter (as in the embodiments) can be combined with one another to form a new or preferred embodiment. Due to space limitations, they will not be mentioned here.

FIGURES

Figure 3:
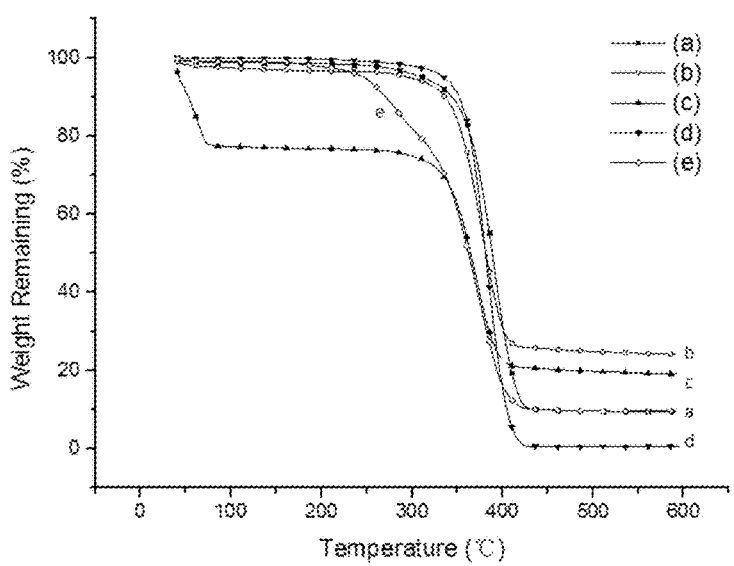

FIG. 3 shows the thermogravimetric analysis of bone cement products 1, 2, 3, and commercially available PMMA bone cement, wherein (a) bone cement product 1, (b) bone cement product 2, (c) bone cement product 3, (d) HEMA-MMA copolymer 2, (e) PMMA sample.

Figure 4:
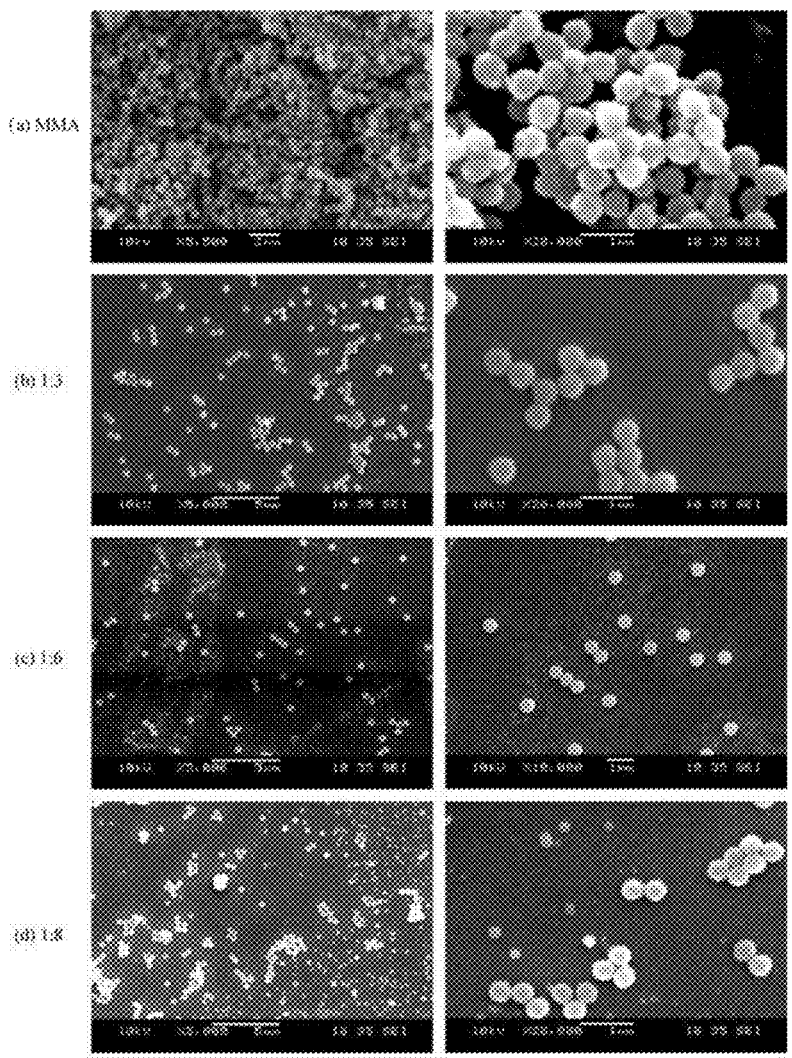

FIG. 4 shows SEM images of the reference sample MMA (FIG. 4a), HEMA-MMA copolymer 1 (FIG. 4b), 2 (FIG. 4c), 3 (FIG. 4d).

FIG. 5 shows SEM images of HEMA-MMA Copolymer 1 attached to calcium phosphate (FIG. 5e), HEMA-MMA Copolymer 2 attached to calcium phosphate (FIG. 5f), and HEMA-MMA copolymer 3 attached to calcium phosphate (FIG. 5g).

FIG. 6 shows test images of the static water/oil contact angle of MMA (reference sample), bone cement product 1, bone cement product 2, and bone cement product 3 (from top to bottom).

Figure 7:
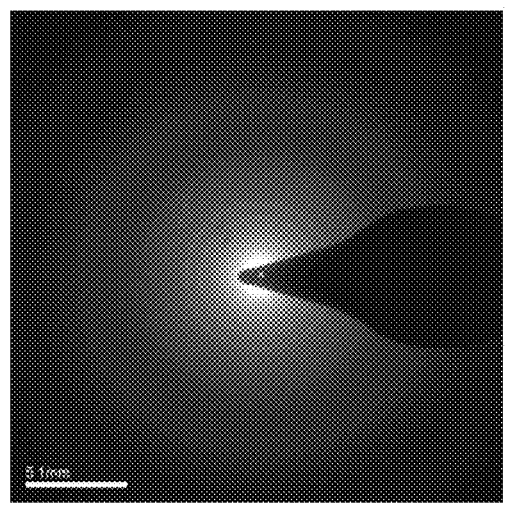

FIG. 7 shows the transmission electron microscopy and selected area electron diffraction images of nano-calcium phosphate coating coated on HEMA/polymethyl methacrylate copolymer.

Figure 8:
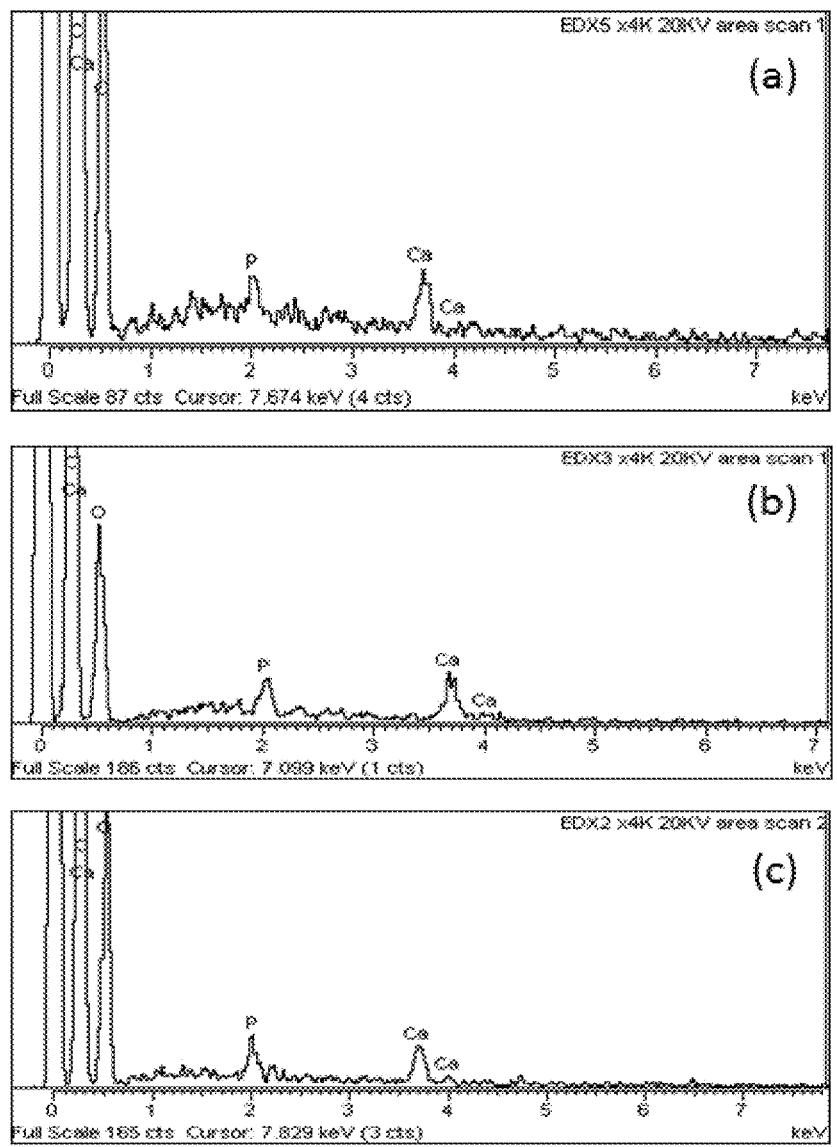

FIG. 8 shows the results of EDX analysis of nano-calcium phosphate coating coated on HEMA/polymethyl methacrylate copolymer. The HEMA:MMA ratio is: (a) 1:3, (b) 1:6, (c) 1:8.

Figure 9:
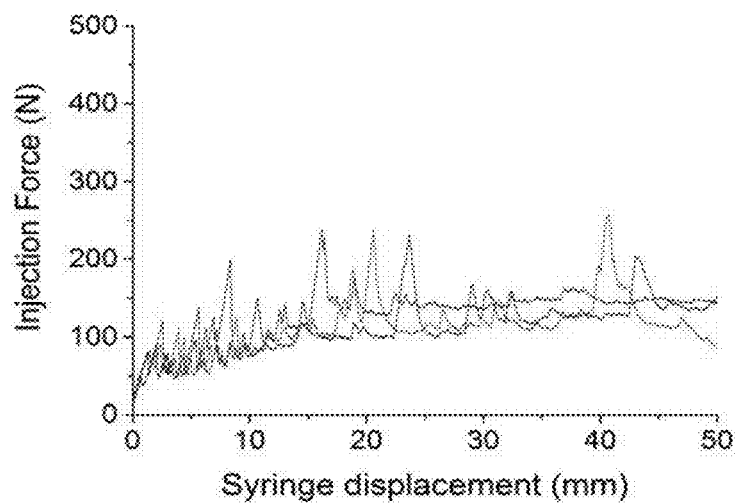

FIG. 9 shows the force-displacement graph of the bone cement extrusion measured using a 21G needle at a 15 mm/min extrusion speed.

Figure 10:
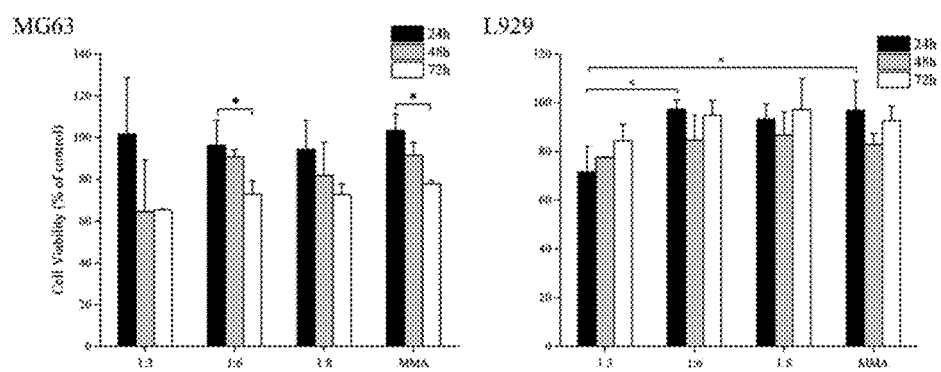

FIG. 10 shows CCK-8 cytotoxicity assays of bone cement product 1, bone cement product 2, bone cement product 3, and MMA using mouse fibroblasts (L929) and human osteoblasts (MG63).

Figure 11:
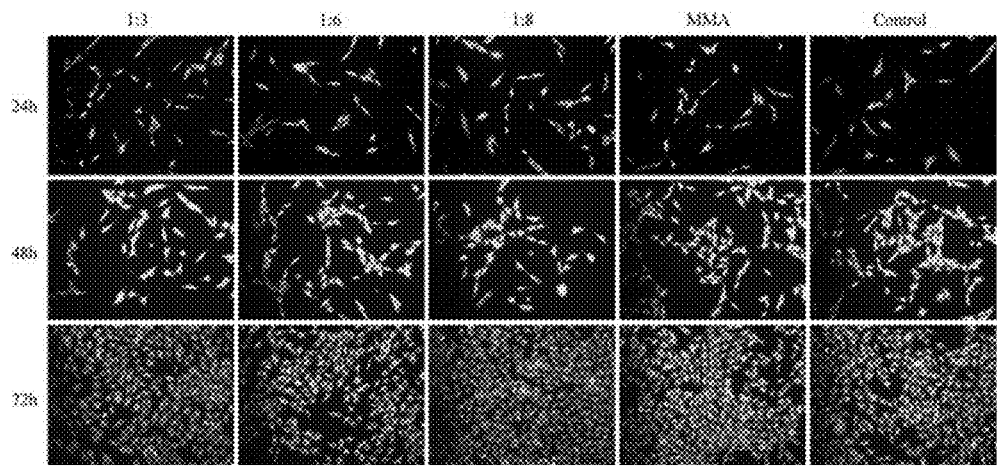

FIG. 11 shows the Live/Dead fluorescent staining of MG63 cell after 24 h, 48 h, and 72 h co-culture.

Figure 12:
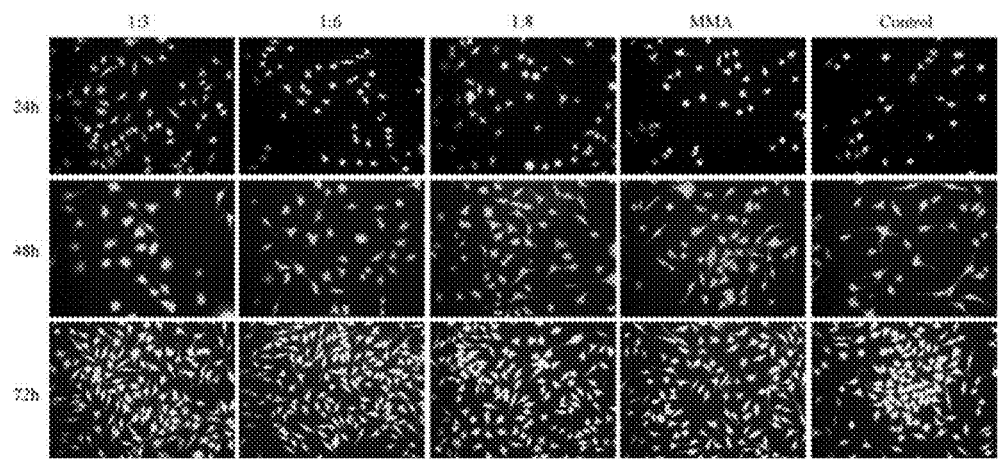

FIG. 12 shows the Live/Dead fluorescent staining of L929 cell after 24 h, 48 h, and 72 h co-culture.

Figure 13:
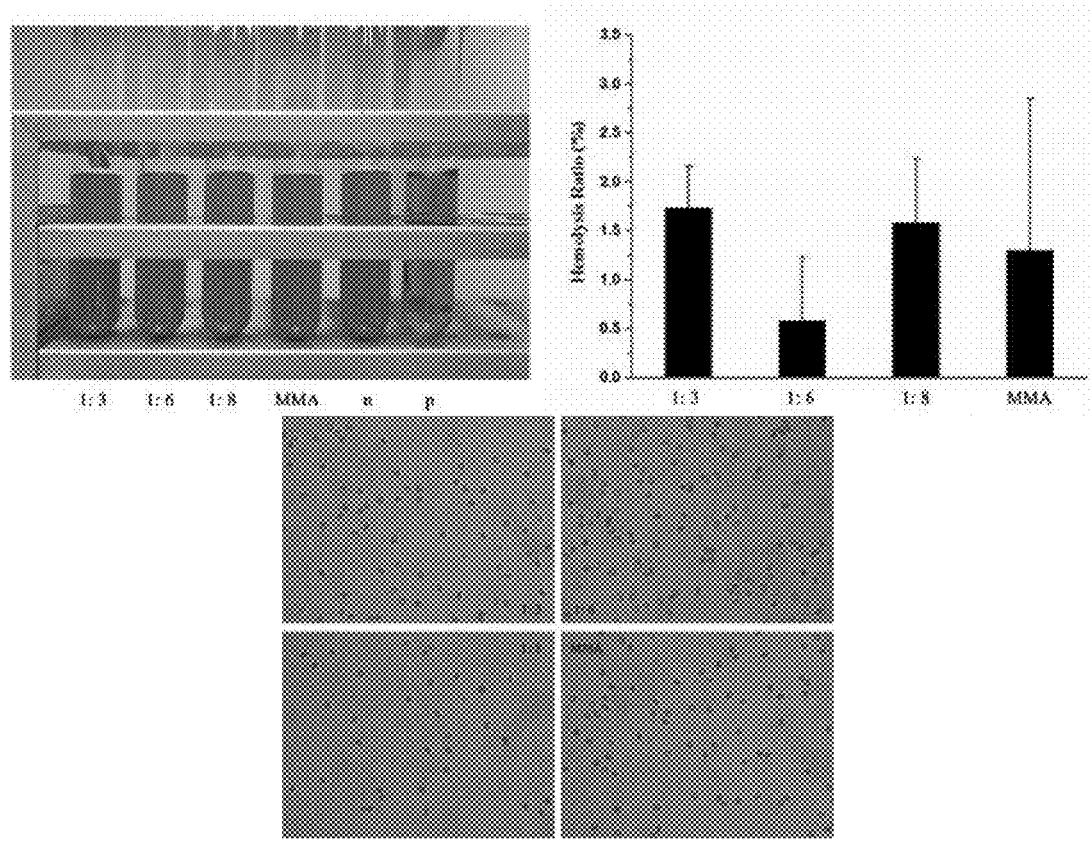

FIG. 13 shows the test results of the hemolysis rate of bone cement product 1, 2, 3 and MMA.

Figure 14:
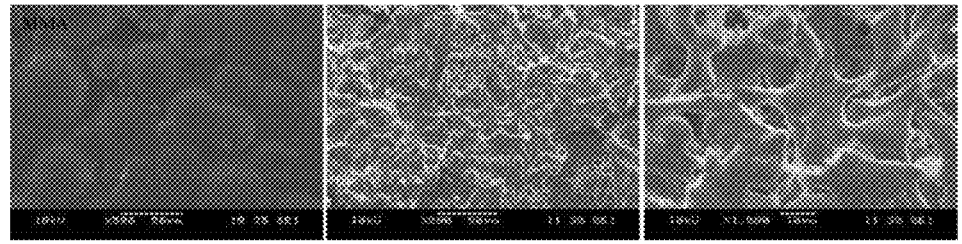

FIG. 14 shows the SEM images of the L929 cell attachment onto commercially available MMA and bone cement product 2.

Figure 15:
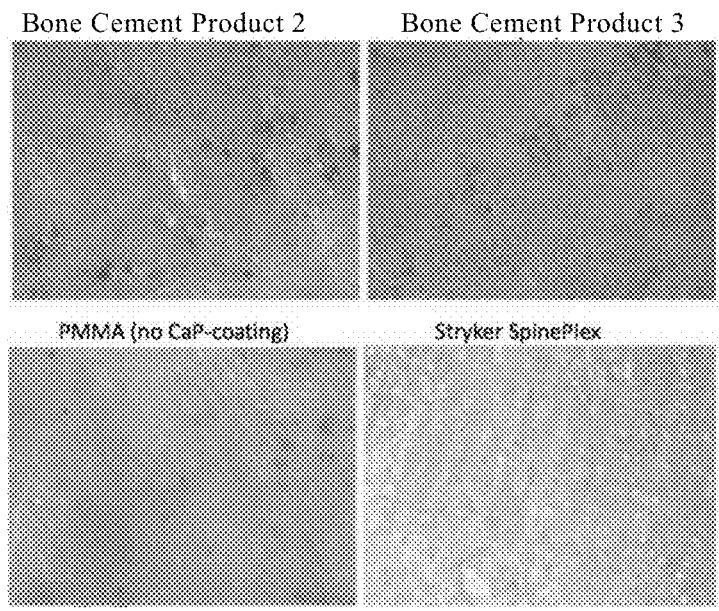

FIG. 15 shows the results of Alizarin Red S. staining for bone cement product 2, 3 and PMMA (not coated with calcium phosphate). Nodules stained in red indicate positive calcium deposition.

Figure 16:
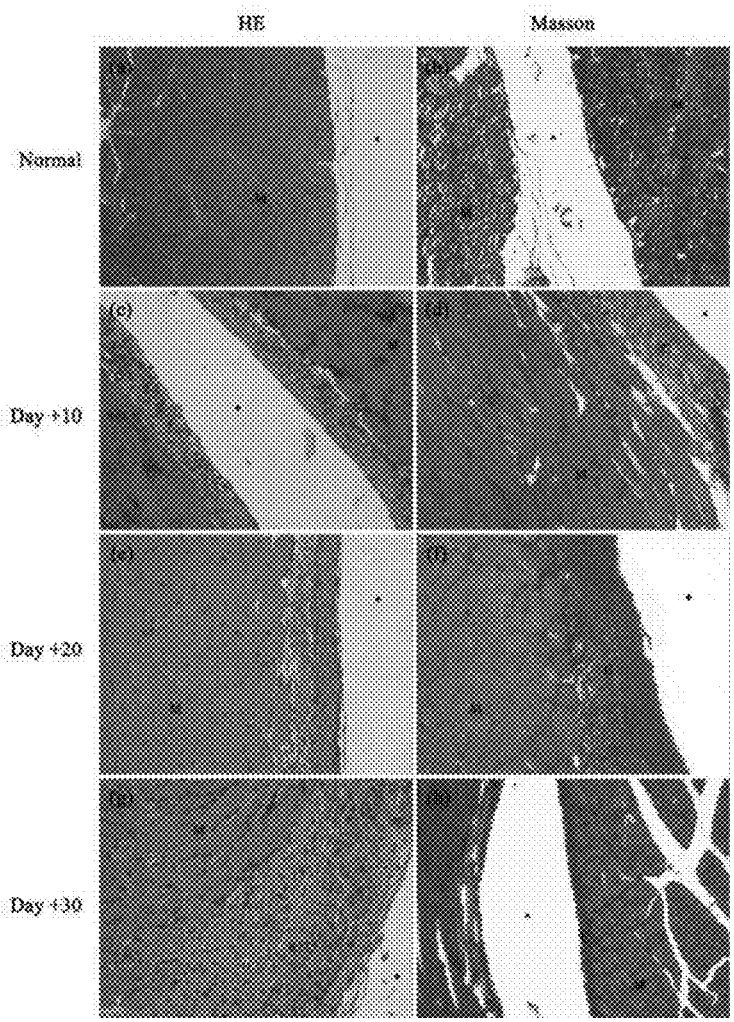

FIG. 16 shows the analysis of rat muscle histopathological staining.

Figure 17:
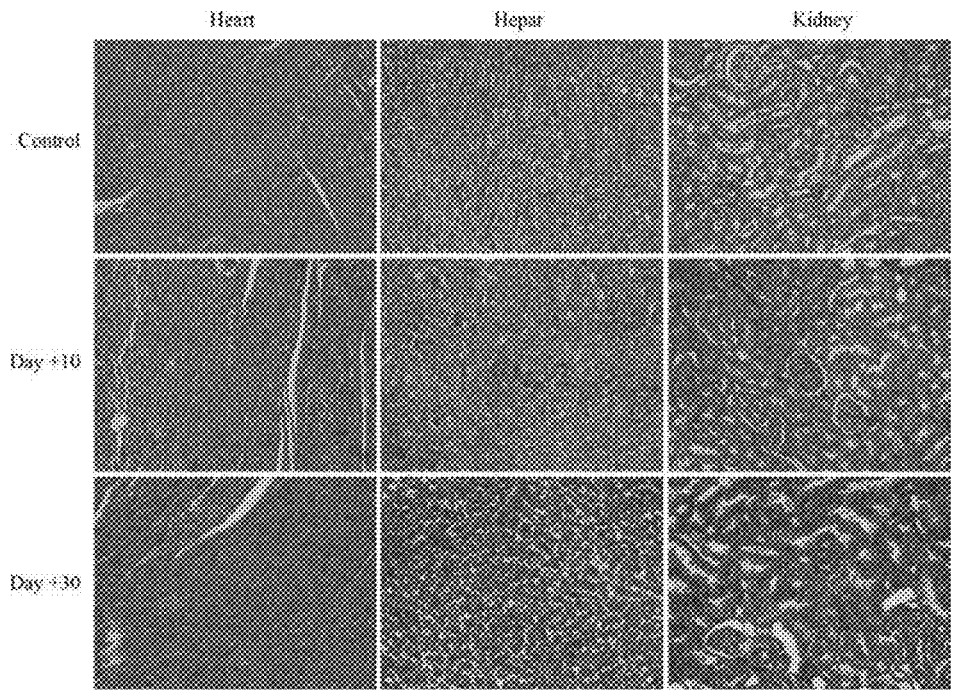

FIG. 17 shows the H&E staining of the human heart, liver, and kidney.

Figure 18:
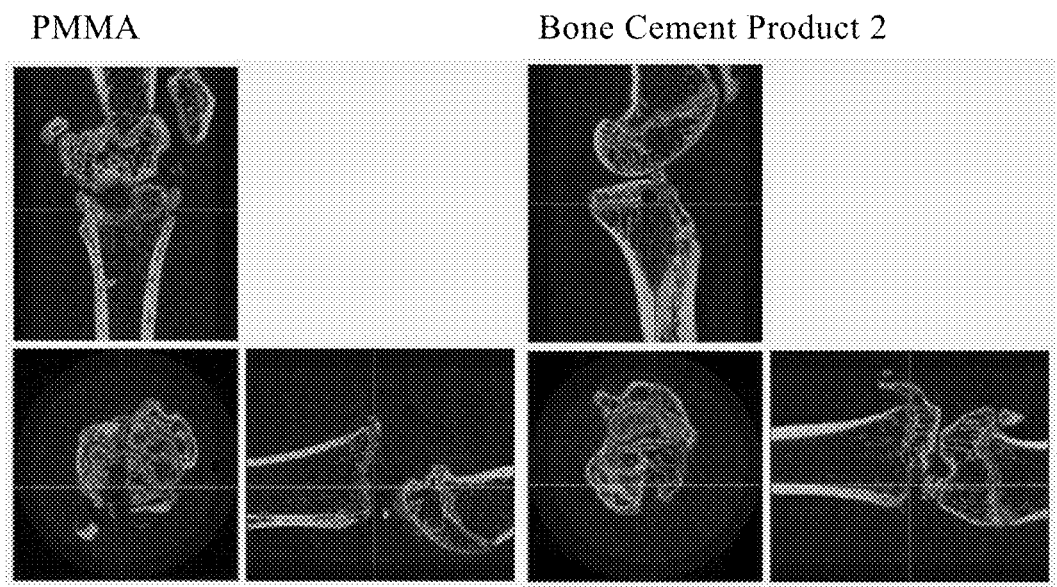

FIG. 18 shows a representation of a Micro-CT scan of the left tibia of a guinea pig.

Figure 19:
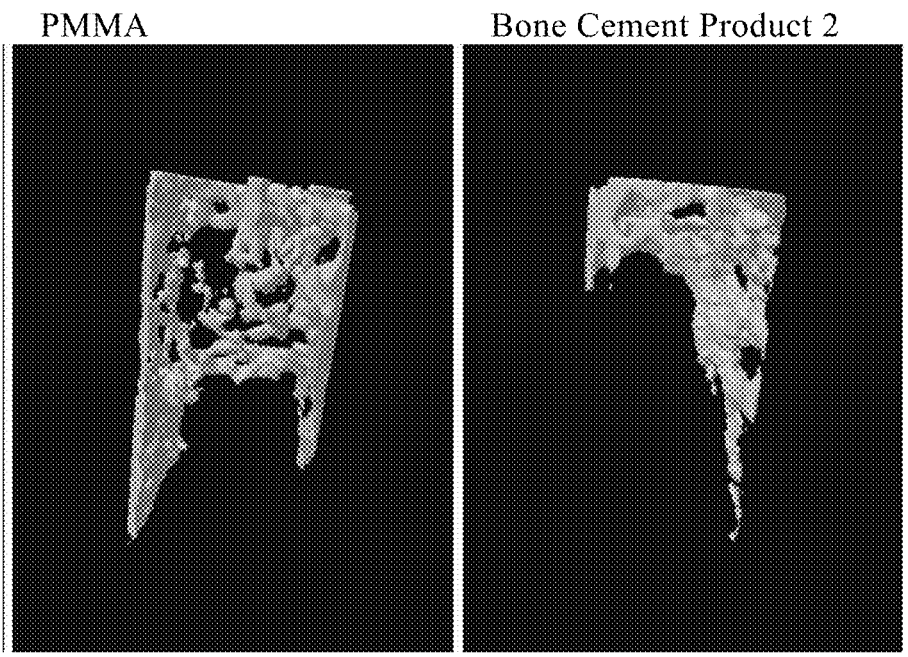

FIG. 19 shows a three dimensional reconstructed model of the Micro-CT scan of guinea pig's left tibia.

Figure 20:
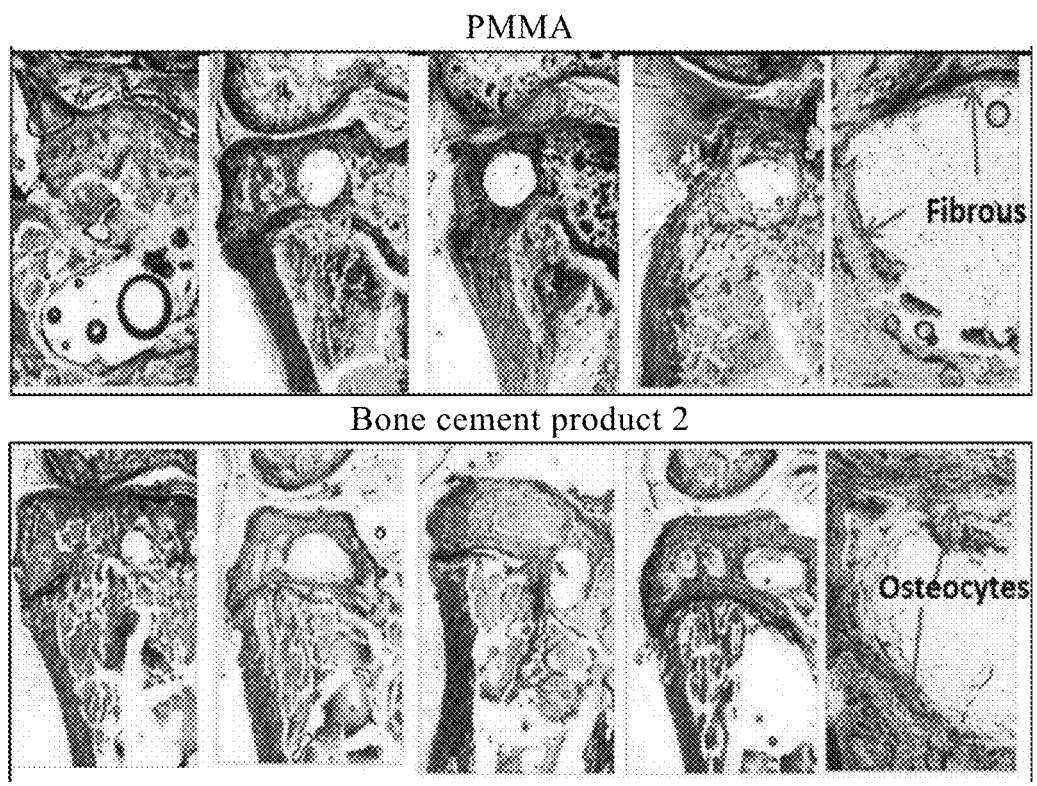

FIG. 20 shows the histological staining of the left tibia of the guinea pig.

DETAILED DESCRIPTION OF THE INVENTION

Through extensive and in-depth research, the inventors have for the first time unexpectedly discovered a new synthetic replacement bone material along with its preparation and application. By adjusting the HEMA-MMA ratio and controlling the thickness and distribution of the calcium phosphate coating of HEMA and MMA copolymer, the biocompatibility and mineralization efficiency of the bone cement have been improved. Furthermore, this invention achieves ultra-low viscosity of the bone cement, allowing the injection using small syringes (21G or smaller) through (1) eliminating the non-adhesive dough state, (2) nanometerizing the formulation components, and (3) changing the formulation polymerization reaction. The features mentioned above signal the completion of my invention.

Terminology

Unless defined otherwise, all scientific terminology used herein have the same meaning as commonly understood by one of ordinary skill in the art to which this invention belongs.

As used herein, when the term "about" is used to describe a value, the value may vary by no more than 1% from the listed value. For example, the expression "about 100" as used herein includes all values of 99 and 101 (eg. 99.1, 99.2, 99.3, 99.4, etc.).

As used herein, the term "containing" or "including" may be open, semi-closed, and closed. In other words, the terms also include "consisting essentially of," or "consisting of."

Calcium Phosphate

As used herein, the terms "calcium phosphate", "CaP" are used interchangeably.

Calcium phosphate can generally be mixed in bone cement or used as a surface treatment coating for bone grafts. This calcium phosphate coating contains hydroxyapatite, which is similar to the composition of natural bone, thus promotes the binding of osteoblasts and bone cement, promotes bone cells to form a new bone, and allows bone cement and bone to fuse together. This effect is also known as the bioactivity of bone cement. In order to give bone cement such bioactivity, a biologically active substance can be added to the bone cement, wherein a part of CaP may be exposed to the solidified cement surface and provide biological activity. Another alternative is to use self-produced body fluids to create a natural bioactive layer on the surface of the bone cement. After implantation, the body fluids surrounding the bone cement or the released material of bone cement itself may form sedimentary deposits. These deposits generally consist of calcium phosphate that is biocompatible and this process is known as mineralization.

Fluidity

The bone material composite granules have excellent fluidity and handling property, the setting time, after the components are mixed, ranges from 10 to 15 mins (preferably 12-15 mins, more preferably 14-15 mins), and can also be administered through 21G syringes or syringes with larger needle diameters (such as 20G, 19G, 18G, 17G, etc.).

The main advantages of the invention are:

(1) The bone material composite granule and bone cement product of the invention comprise a copolymer of mixed hydroxyethyl methacrylate and methyl methacrylate with better biological activity physically coated with a layer of calcium phosphate. The polymer-based solid material can be formed in a short time under control. The resulting bone grafts has excellent stability in the body coupled with good mechanical strength.

(2) The bone material composite granule and bone cement product of the invention have excellent fluidity and handling property. The bone cement also has ultra-low viscosity and enhanced rheological property without non-adhesive dough stage, which facilitates injections through small syringes (e.g., syringes with a diameter of about 0.5 mm or less (e.g., 21G)). The bone material composite granule and bone cement product of the invention can be injected through a larger syringe (e.g., 18G or larger) at a later stage after mixing certain ingredients to suit the requirements of specific surgery conditions.

(3) The bone material composite granule and bone cement product of the invention can be sterilized by radiation or gas without changing their properties.

(4) The bone material composite granule and bone cement product of the invention can be applied to maxillofacial surgery, plastic surgery, spinal surgery, etc., such as bone necrosis, osteoporosis, alveolar bone atrophy, osteoarthritis, subchondral bone defects, etc., and can be applied to vertebroplasty, maxillofacial surgery, and plastic surgery.

Raw Materials

Commercially available PMMA bone cement:

Spineplex radiopaque bone cement (purchased from Stryker Corp):

40 g powder (4.7 g polymethyl methacrylate, 23.3 g MMA-styrene copolymer containing benzoyl peroxide (1.5%), 12 g of barium sulfate); and 20 ml liquid (19.5 ml MMA, 0.5 ml N, N-dimethyl-p-toluidine, 1.5 mg hydroquinone).

Setting time 8.2 min, 10-14G syringe

MMA:

Methyl methacrylate ([Wako/139-027261]) (MMA, 98+%, containing 0.005% hydroquinone General Methods 1. Fourier infrared spectroscopy (FTIR) analysis 2. Nuclear magnetic resonance spectroscopy (NMR)

The sample analysis was performed using a German Bruker AV 400 nuclear magnetic resonance (NMR) machine. Tetramethylsilane (TMS) was used as the internal standard, and the sample was dissolved in deuterated dichloromethane. A nuclear magnetic resonance spectrum ($^1$H NMR spectrum) was obtained by scanning 32 times at normal temperature at a frequency of 400 MHz.

3. Granule Size Distribution Analysis

Granule size was measured using Zetasizer Nano dynamic light scattering. A small amount of the sample was placed in deionized water. The resulting solution was transparent and the test was performed 2 hours after ultrasonication.

4. TGA Thermogravimetric Analysis

The thermal stability of the material was measured using a thermogravimetric analyzer (Q50, TA, USA).

Test method: The instrument must be zeroed before loading. 3-10 mg of pre-dried sample was weighed and placed on the platinum plate. Temperature was increased from room temperature to 600° C. (the sample was completely decomposed), and the heating rate was 10° C./min. Under the protection of nitrogen, the sample gas diffused at 40 mL/min, and the equilibrium gas diffused at 60 mL/min. The temperature at which the sample loses weight by 10 wt % is defined as the thermal decomposition temperature of the material.

5. Scanning Electron Microscopy (SEM) Analysis

The scanning electron microscope (SEM) was used to observe the morphology and the form of uncured, white powder before and after being coated with CaP.

6. Static Water Contact Angle Test

The contact angle refers to the angle between the tangential lines of the gas-liquid curve and the solid-liquid curve intersecting at the triple point.

When $\theta<90°$, the solid surface is hydrophilic, meaning that the liquid is easier to wet the solid. A smaller contact angle indicates a higher wettability of the solid surface.

When $\theta>90°$, the solid surface is hydrophobic, indicating that the solid surface has low wettability.

Static contact angle test of the samples was performed by the contact angle analyzer (SL600, Solon Information Technology Co, Shanghai, China). Under normal temperature and pressure conditions, the samples were placed on the test platform and the relevant parameters of the software settings were set. 4 μl of deionized water and diiodomethane were held in place, respectively and 7 samples were randomly selected. The samples were brought into contact with the water and diiodomethane. The contact angle was measured and the light intensity was observed and adjusted according to the video captured images. The data and the images were recorded, and the average value was taken as the static contact angle value of the material.

Sample preparation: The material were mixed according to the ratio listed in the setting reference table. The mixture was spread on a glass sheet in a thin paste form thereby forming a rectangular sheet.

7. Transmission electron microscopy and selected area electron diffraction images of HEMA-polymethyl methacrylate copolymers coated with nano-CaP The Cap coating and crystallographic properties of crystal samples were observed by transmission electron microscopy (TEM) and selected area electron diffraction images and the in-situ analysis of the morphology was conducted.

8. EDX analysis of HEMA/polymethyl methacrylate copolymers coated with nano-CaP

Element Analysis was performed with Transmission Electron Microscopy (TEM) with Energy Dispersive X-Ray Spectroscopy The invention is further illustrated below with examples. It is to be understood that the examples are for illustrative purposes only and are not intended to limit the scope of the invention. The experimental methods listed in the following examples, which do not specify the testing conditions, were generally carried out under conventional conditions or according to the conditions recommended by the manufacturer. The percentages and ratios, unless otherwise stated, are mass or weight related.

The experimental materials and reagents used in the following examples are commercially available unless otherwise specified.

EXAMPLE 1

Bone Cement Product 1

1.1 HEMA-MMA Copolymer 1 (HEMA-MMA=1:3 (wt %)) was Prepared by Emulsion Polymerization Method 6.0 ml HEMA (95% concentration) and 17.2 ml MMA (98% concentration) monomers were added to 120 ml of potassium persulfate solution (concentration: 0.00133 g/cm$^3$), and heated to 80° C. under nitrogen. The solution was continuously stirred for 3 hours to obtain HEMA-MMA copolymer 1.

1.2 HEMA-MMA Copolymer 1 is Attached with Calcium Phosphate

HEMA-MMA copolymer 1 obtained in 1.1 were added to 450 ml Ca(OH)$_2$ solution (concentration: 0.0085 g/cm$^3$). While stirring constantly, 7.5 ml of H$_3$PO$_4$ solution (concentration 20%) was added. The dispersion rate of the H$_3$PO$_4$ solution was 0.139 ml/hour and the solution was stirred constantly until the solution was neutral. The obtained crude product was centrifuged at 7,800 rpm for 15 minutes, washed, and the water in the product was sublimed through lyophilization thereby dehydrating the crude product to obtain PMMA-HEMA/CaP powder I.

1.3 Setting of HEMA-MMA/CaP Bone Cement

At room temperature, 10 g of crude benzoyl peroxide, BPO, was weighed and dissolved in 40 ml of chloroform, and the precipitate was filtered. The filtrate was poured into 100 ml of methanol, which was cooled in advance in an ice salt bath. The crystal needles were precipitated, suction filtered, and dried under reduced pressure with calcium chloride to obtain a purified product.

7.5 g of PMMA-HEMA/CaP powder I, 0.8 g of BPO, and 0.16 g of BaSO$_4$ (mass ratio about 1:1:0.2) were weighted, respectively, and then coarsely grinded and mixed evenly. 25 ml of MMA and 0.25 ml of DMPT mixed solution (MMA: DMPT volume ratio was 1:0.01) were added and stirred at uniform speed in the same direction for about 2 minutes. The mixture was slowly aspirated with a syringe, tapped on the tube wall to remove the bubbles, and injected into a mold.

EXAMPLE 2

Bone Cement Product 2

2.1 HEMA-MMA Copolymer 2 (HEMA-MMA=1:6 (wt %)) was Prepared by Emulsion Polymerization Method.

Same as 1.1 of Example 1, except that HEMA was 3.8 ml and MMA was 19.6 ml.

Steps 2.2 and 2.3 are the same as in Examples 1.2 and 1.3.

EXAMPLE 3

Bone Cement Product 3

3.1 HEMA-MMA Copolymer 3 (HEMA-MMA=1:8 (wt %)) was prepared by emulsion polymerization method Same as 1.1 of Example 1, except that HEMA was 2.8 ml and MMA was 20.4 ml.

Steps 3.2 and 3.3 are the same as in Examples 1.2 and 1.3.

COMPARATIVE EXAMPLE 1

Cement Product C1

C1.1: HEMA-MMA Copolymer C1 (HEMA-MMA=1:2 (wt %)) was Prepared by Emulsion Polymerization Method Same as 1.1 of Example 1, except that HEMA was 8.4 ml and MMA was 14.6 ml. Steps C1.2 and C1.3 are the same as in Examples 1.2 and 1.3.

COMPARATIVE EXAMPLE 2

HEMA-MMA Copolymer C2

Similar to Example 2.1, except that only HEMA-MMA copolymer C2 was prepared without calcium phosphate coating.

Result Analysis

Figure 1:
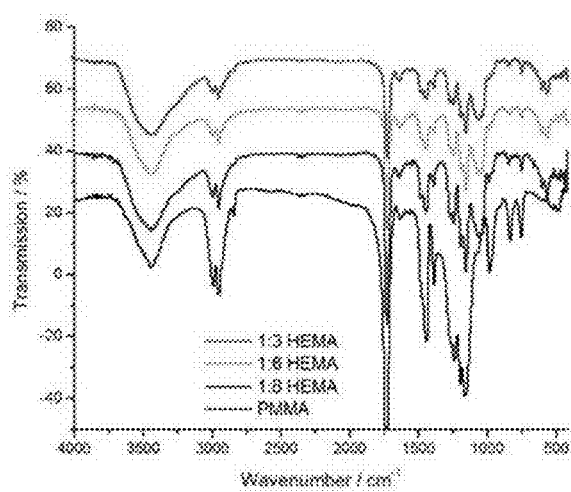
FIG. 1 shows Fourier-Transform infrared spectra of bone cement products 1, 2, 3, and commercially available PMMA bone cement from top to bottom, respectively.

1. The Fourier transform infrared spectrum of bone cement products 1, 2, 3, and commercially available PMMA bone cement materials are shown in FIG. 1. A comparison of the four sets of spectra shows:

2991 cm$^{-1}$ is the stretching vibration peak for $CH_3$, 2950 cm$^{-1}$ is the stretching vibration peak for $CH_2$, 1750 cm$^{-1}$ is the stretching vibration peak for C=O, 1436 cm$^{-1}$ is the bending vibration peak for H—C—H, 1270~1100 cm$^{-1}$ is the vibration peak for C—O, and the 700 cm$^{-1}$ peaks are the out-of-plane vibrations of H—C—H. The peaks in the four spectra listed above are not changed after adding CaP to the products. The figure shows that the addition of calcium phosphate has no effect on the peaks of the infrared spectrum of the bone cement products.

The absorption peak at 3480 cm$^{-1}$ is the O—H stretching vibration peak of the modified monomer HEMA. The appearance of this absorption peak indicates that the modified monomer participates in the polymerization of polymethyl methacrylate. This proves that the added HEMA monomer is polymerized with MMA.

Figure 2:
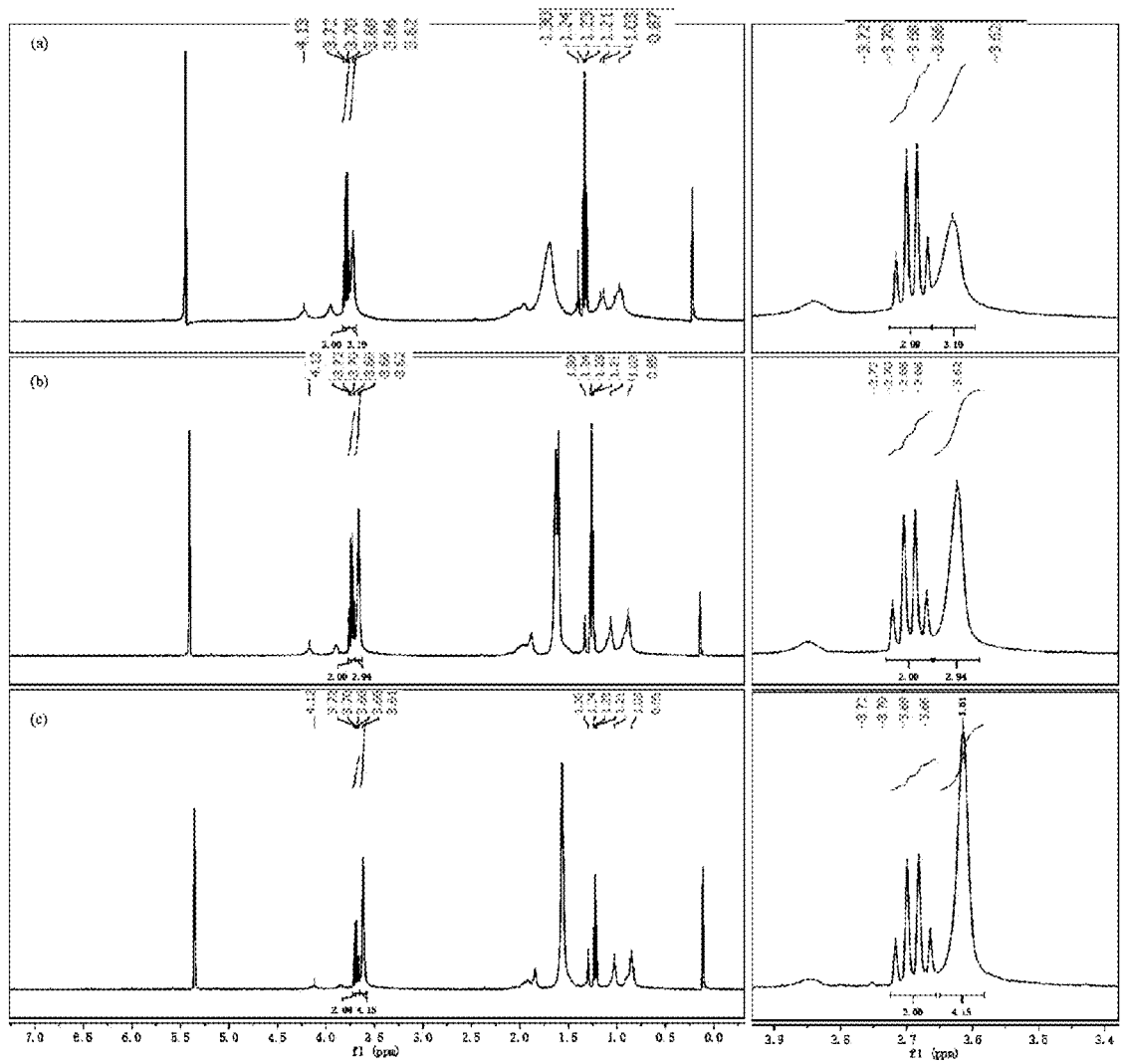
FIG. 2 shows NMR spectra of HEMA-MMA copolymer 1 (FIG. 2a), 2 (FIG. 2b), and 3 (FIG. 3c).

2. The nuclear magnetic resonance spectra of HEMA-MMA copolymer 1 (FIG. 2a), 2 (FIG. 2b) and 3 (FIG. 2c) are shown respectively in FIG. 2. The chemical structures of the HEMA-MMA copolymers are characterized by $^1$H NMR spectra. It can be seen from FIGS. 2a-2c that all proton peaks on the HEMA-MMA copolymers can be accounted by the nuclear magnetic resonance H-spectrum. Based on the characteristic proton peak integral area ratio of the HEMA and MMA repeating units, the m/n value of the HEMA-MMA copolymer can be calculated. The number average molecular weight of the HEMA-MMA copolymer can then be calculated by the following formula:

$$M_n = M_{MMA} \times \frac{2Q}{3P} + M_{HEMA}$$

wherein, $M_{MMA}$ denotes the molecular weight of a MMA molecule and $M_{HEMA}$ denotes the molecular weight of a HEMA molecule. Q denotes the integral area of the characteristic peak of MMA unit (—COOC$\underline{H}_3$—, δ6.10 ppm) and P denotes the integral area of the characteristic peak of HEMA unit (—C$\underline{H}_2$OH, δ3.68 ppm). The number average molecular weight of the HEMA-MMA polymer is shown in Table 1.

TABLE 1

Number Average Molecular Weight of HEMA-MMA copolymer

| | HEMA:MMA ratio | | |
|---|---|---|---|
| | 1:3 | 1:6 | 1:8 |
| $M_n$ | 203.23 | 228.26 | 268.64 |

3. As shown in the thermogravimetric analysis chart of FIG. 3, there was no significant change in thermal stability when comparing the modified bone cement to commercially available bone cement. The thermal decomposition curve of bone cement product 3 showed in (c) has two decomposition steps. The first decomposition step may be the decomposition of unreacted MMA monomers. The HEMA-MMA copolymer 2 in (d) contains only the elements C, H and O. According to the Figure, the amount of calcium phosphate attached to the modified bone cement can be compared, which is (b)>(c)>(a).

4. Granule size distribution results:

(1) HEMA-MMA copolymer 1 has an average granule size of 759.7 nm;

(2) HEMA-MMA copolymer 2 has an average granule size of 509.8 nm;

(3) HEMA-MMA copolymer 3 has an average granule size of 585.2 nm;

(4) HEMA-MMA copolymer C2 has an average granule size of 180.1 nm;

The results show that the diameters of CaP coated copolymers are significantly larger than the diameters of HEMA-MMA copolymers without CaP coating.

5. SEM Analysis

The SEM images of reference sample MMA (FIG. 4a), HEMA-MMA copolymer 1 (FIG. 4b), 2 (FIG. 4c), 3 (FIG. 4d), bone cement product 1 (FIG. 5e), 2 (FIG. 5f), and 3 (FIG. 5g) are shown in FIG. 4 and FIG. 5. The CaP coating amount and granule size are shown in Table 2.

TABLE 2

| Number | Sample | CaP coating amount (g) | Granule Size (nm) |
|---|---|---|---|
| 1 | MMA (reference sample) | — | |
| 2 | Bone cement product C1 | 1-2 | 954 ± 223 |
| 3 | Bone cement product 1 | 1-2 | 629 ± 139 |
| 4 | Bone cement product 2 | 1-2 | 596 ± 167 |
| 5 | Bone cement product 3 | 1-2 | 405 ± 103 |

6. Static Water Contact Angle Test Results

FIG. 6 shows static water/oil contact angle for MMA (reference sample), bone cement product 1, bone cement product 2, and bone cement product 3. The angle data is shown in Table 3.

TABLE 3

| Number | Water Contact Angle (°) | Oil Contact Angle (°) |
|---|---|---|
| MMA (reference sample) | 91.18 ± 2.5 | 41.31 ± 3.3 |
| Bone cement product 1 | 67.72 ± 1.1 | 29.79 ± 3.1 |
| Bone cement product 2 | 76.69 ± 1.8 | 36.32 ± 1.4 |
| Bone cement product 3 | 82.83 ± 2.1 | 35.87 ± 1.8 |

7. Transmission electron microscopy and selected area electron diffraction (SAED) images of the nano calcium phosphate coating on HEMA/polymethyl methacrylate copolymer The interplanar spacings are calculated from the diffraction rings as shown in FIG. 7 in the selected area electron diffraction table (Table 3). The diffraction patterns of the sample match the standard crystallographic diffraction pattern of hydroxyapatite, showing hydroxyapatite crystals are present in the coating.

TABLE 4

| Point | interplanar spacing (nm) | Reciprocal of spacing (1/nm) | Angle relative to Point 1 | Angle relative to the x-axis | Arc Length |
|---|---|---|---|---|---|
| 1 | 0.3462 | 2.888 | 0.00 | 139.68 | 2548.00 |
| 2 | 0.3226 | 3.100 | 0.07 | 131.61 | 1792.00 |
| 3 | 0.2818 | 3.548 | 4.13 | 135.55 | 1795.00 |
| 4 | 0.2713 | 3.686 | 8.30 | 131.38 | 1642.00 |
| 5 | 0.1919 | 5.211 | 6.06 | 145.74 | 921.00 |
| 6 | 0.1857 | 5.384 | 0.58 | 139.10 | 741.00 |
| 7 | 0.1747 | 5.724 | 3.33 | 136.55 | 633.00 |

8. The force-displacement curve of the bone cement was measured using a 21G needle at an extrusion rate of 15 mm/min. The data is shown in Table 4.

TABLE 4

| Number | Bone Cement | Setting Time | Maximum reaction temperature (° C.) | Syringe | Bending Strength (MPa) | Compressive Strength (MPa) |
|---|---|---|---|---|---|---|
| 1 | PMMA | 10-12 | >90° C. | — | — | — |
| 2 | Bone cement Product C1 | Cannot solidify and poor handling properties | | | | |
| 3 | Bone Cement Product 1 | 10-15 | 75-80 | Injectable with >21 G needle | >50 | >90 |
| 4 | Bone Cement Product 2 | 10-15 | 70-75 | 21G | >50 | >100 |
| 5 | Bone Cement Product 3 | 10-15 | 65-70 | 21G | >50 | >100 |

9. CCK-8 Cytotoxicity Test

The effects of different proportional acrylic bone cement formulations after hydrophilization on bone cells were evaluated by CCK-8 cytotoxicity and hemolysis tests.

The test data were processed using SPSS (19.0) statistical software, t-test analysis (significant differences of $*p<0.05$, $p<0.005$, $*p<0.0005$).

Mouse fibroblasts (L929) and human osteoblasts (MG63) were selected to study the biocompatibility of bone cement materials and cell viability was tested with CCK-8.

Experimental procedure: A cell suspension was inoculated into a 24-well plate, with a cell count of about 10,000 cells/ml and about 200 μl per well and 1 ml of medium was added. Bone cement product 1, bone cement product 2, bone cement product 3, and MMA were set as experimental groups in 4 wells each. 4 wells with just the medium as the culture control group and 4 blank wells as blank control group were also set.

The cell cultures were placed in a 37° C. incubator for 6 hours and a pre-UV sterilization sample (size about 3*3 mm) was added. The cell cultures were then incubated at 37° C. for 24 h/48 h/72 h. Then, 200 μl of CCK-8 working solution was added to each well and incubated for 90 mins. The metabolic activity of the cells was measured by a microplate reader. The absorbance was measured at 450 nm.

10. Fluorescent Staining

Calcein-AM was used in combination with EthD-1 to simultaneously stain fluorescent cells and dead cells.

Staining steps: DPBS was used to prepare a staining solution with a concentration of 2 μM Calcein-AM and 4 μM EthD-1; Cells were washed twice with DPBS to eliminate or to reduce serum phenolase activity (serum phenolase can hydrolyze Calcein-AM to increase extracellular fluorescence intensity); 150 μl of staining solution was added at room temperature for 20 minutes or for 10-15 minutes at 37° C.; The cells were then photographed by fluorescence microscopy. As shown in FIGS. 11 and 12, according to the results of LIVE/DEAD staining, the number of cells in MG63 and L929 cells was not significantly different at 24 h. However, the cell morphology was thinned and the cells did not completely protrude from the pseudopod, seemingly caused by the bone cement formula. After 48 h, the cell morphology of each group was basically the same as that of the blank group, indicating a good cell state. Although no obvious dead cells were observed, the cell number was still low and the cell proliferation rate had slowed down. This indicated that the bone cement may have inhibited cell proliferation. After 72 h, the cell proliferation rate increased significantly, and the cell morphology was normal.

11. Hemolysis Rate Experiment

Bone cement products 1, 2, 3 materials were prepared into 5*5 mm sheets. They were UV sterilized for 3 hours. After sterilization of these materials, they were washed with sterile ultrapure water 3 times and then washed with PBS or saline 3 times. The materials were then transferred into sterile tubes with 10 ml of saline and incubated with shaking in an incubator shaker at 37° C. for 60 min.

Blood samples were prepared by diluting whole blood with normal saline to a ratio of 4:5 after treating the blood with anticoagulants.

The sample control (AS): a 0.2 ml blood sample was added to the test tubes in the incubator; and the tubes were incubated with shaking for another 60 min.

The positive control (AP): 10 ml ultrapure water+0.2 ml blood sample was incubated with shaking for 60 min.

The negative control (AN): 10 ml saline+0.2 ml blood sample was incubated for 60 min with shaking; and the solution was then centrifuged at 800 rpm for 5 min. The supernatant was taken, and the absorbance was measured at 540 nm using a spectrometer to calculate the hemolysis rate (HR).

$$HR = \frac{AS - AN}{AP - AN} \times 100$$

As shown in FIG. 13, the hemolysis ratio (HR) of red blood cells can reflect the blood compatibility of the material. The hemolysis rate indicates the amount of red blood cell breaking down when in contact of the sample. The higher the hemolysis rate, the more red blood cells are broken down. Therefore, a lower hemolysis rate indicates the sample has a better blood compatibility. Medical standards require biomaterials to have a hemolysis rate less than 5%. The data shows that all of the bone cement products pass the medical standards and in particular, bone cement product 2, HEMA-MMA (1:16)/CaP, has the best blood compatibility.

12. Cell Attachment Experiment

200 μl of high-concentration cells were dropped in the center of the bone cement material sample and incubated at 37° C. for 6 hours. Then, 1.5 ml of the culture solution was added and the sample was incubated for another 24 hours. The sample was taken out of the incubator and washed three times with PBS. A pre-cooled fixative (2.5% glutaraldehyde) was added to sample and placed in a refrigerator at 4° C. for 3 hours. The sample was then taken out of the refrigerator, rinsed three times with distilled water, and dried in a freeze dryer for 24 hours or more. The sample was fixed on a workbench with a conductive paste and observed through a scanning electron microscope (SEM).

As shown in FIG. 14, L929 cells were selected for the experiment to detect the amount of cells bonded to bone cement. After the cells were inoculated on the bone cement and cultured for 12 hours, the SEM results showed that the cells were well attached to the bone cement and the cells' morphologies were normal. Compared with the commercially available PMMA bone cement, the modified bone cement is more suitable for cell growth and compatibility. The beneficial properties of the bone cement material may help L929 cells form a variety of three-dimensional structures to form organizational functions.

13. Biomineralization Reaction Test

The cells cultured in this experiment formed mineralized nodules on the surface of the bone cement under conditioned medium. The purpose of the mineralization test is to discover the content of calcium salts on the bone cement by staining the samples with Alizarin Red S, which colors the cells red if a calcium deposition is detected. The appearance of orange red mineralized nodules after staining with Alizarin Red S indicates that the material is bioactive. 70,000 cells were seeded on each sample in a culture dish. After 14 days of culturing, the culture solution was removed and the culture dish was washed with a buffer solution. The sample was fixed at room temperature for 60 minutes with 2.5% glutaraldehyde, which was diluted in dimethyihydrazine buffer. After removal of the fixative, the culture dish was rinsed twice with deionized water and alcohol was added for dehydration. 2% Alizarin Red S solution was added for 2 minutes and rinsed with deionized water. The above steps were repeated twice until the orange-red marks appeared and were observable under a microscope.

As shown in FIG. 15, the bone cement products that were coated with calcium phosphate exhibited more orange-red areas. This indicates a better mineralization reaction and favorable bone and cement fusion.

14. Pathohistological staining analysis of rat back muscle: bone cement product injected into rat back muscle Ten adult SD rats, weighing between 150 and 200 g, were embedded bone cement products in the subcutaneous tissues after one week in the experimental animal house.

The rats were first anesthetized with ether, weighed, and then intraperitoneally anesthetized with 10% chloral hydrate equivalent based on its weight. After the rats were completely comatose, the hair on the rat's back was removed and then the exposed skin was disinfected with iodine. The iodine was wiped off with rubbing alcohol. The skin was surgically incised to expose the muscle. An incision with about 8 mm in diameter was made on the back muscle. Pre-sterilized bone cement product 2 (size about 5*5 mm) was put into the muscle layer. The layers were carefully sutured and the blood was cleaned off the body. The rats were held in separate cages to prevent them from biting each other, creating a natural experimental environment. Rats were given penicillin via the abdominal cavity within 3-4 days after surgery to prevent inflammation of the wound.

After 8 weeks, the rats were euthanized. The muscle tissues that had come into contact with the bone cement product and materials were carefully cut out into appropriate shapes with a scalpel. The heart, liver, spleen, kidney and lungs were also harvested.

The excised tissue was placed in a 50 ml centrifuge tube and fixed with Bouin's fixative for 24 hours. The remaining tissues were immersed in 4% paraformaldehyde solution for 24 hours.

Dehydration: each tissue was soaked with distilled water, 50%, 70%, 80%, 90%, 95%, 100% (I). 100% (II) concentration of ethanol for gradient dehydration for 30 min a time.

Clearing: Each muscle tissue was sequentially immersed in ethanol and xylene 1:1 solution, xylene (I) and xylene (II) for 30 min a time.

Infiltration: The muscle tissues were dipped three times in paraffin wax at 40 min a time. The paraffin-infiltrated tissues were then placed on a rack and embedded into wax blocks. The blocks were then placed and sectioned with a microtome. The sections were then flattened with a brush and expanded on the stretcher. The best section was selected and placed on a slide. The slide was dried on a hot plate.

Gradient Dewaxing: The slides were sequentially immersed in xylene (I) and xylene (II) (10 min each), 100% (I), 100% (II), 90% (I), 90% (II), 80%, 70%, 50% ethanol solution (each 5 min) and washed with distilled water for dewaxing.

H&E staining: The slides carrying the tissue sections were stained with hematoxylin solution. After 15 min, the excess hematoxylin solution was removed. The color was differentiated with diluted hydrochloric acid and rinsed off with distilled water. The slides were then counterstained with Eosin solution for 10 min.

Masson trichrome staining: The muscle tissue slides were stained with iron hematoxylin solution for 15 min and then rinsed with distilled water. Muscle tissues were washed with differentiation solution for 2 s, then water for 1 min, and bluing 3 s. After washing the muscle tissues, they were then stained with Ponceau red magenta solution for 10 min and washed again with distilled water for 1 min. The tissues were then treated with 1% phosphotungstic acid solution and observed under microscope during the color development process. The staining process was complete when the muscle appeared red and collagen fibers appeared light red under the microscope. The muscle tissues were washed with water, then counterstained with aniline blue staining solution (for collagen fiber) for 1 min. The tissues were then washed with water and differentiated with 95% ethanol. 100% ethanol was used to dehydrate the muscle tissues, which were then sealed in a plastic cover.

Microscopy: A fluorescence/phase contrast microscope, Eclipse TE 2000, was used to observe and photograph the tissue sections. The collagen fibers and nucleus are blue while the cytoplasm, muscle fibers and red blood cells are red.

As shown in FIG. 16, the bone cement product 2 has a thin layer of collagen fiber at the implantation site.

After 10 days of the bone cement implantation, there were more neutrophils and lymphocytes infiltration. Loose tissue was formed at the contact site between the bone cement material and the muscle tissue. The collagen fiber layer at the edge of the contact site increased while the muscle cells did not change compared with the normal tissue.

20 days after the implantation, there was still a small amount of lymphocyte infiltrating the bone cement product. The bone cement and muscle tissue were tightly bound. The dense fibrous collagen layer was wrapped on the surface of the bone cement product. The muscle tissue at the implant site grew well and the muscle cell morphology was normal.

30 days after the implantation, there was no inflammatory cell infiltration at the implant site, the fibrous tissue did not continue to thicken, and the muscle tissue growth was normal. According to the experimental results, the surface of the bone cement product 2 could form a layer of collagen and the surrounding tissue and cells grew normally. No lesions and allergic reactions were detected, illustrating the biocompatibility of the bone cement product to muscle tissue.

15. Histopathological staining analysis of heart, liver and kidney of rat

The test animals were euthanized by injecting an excessive amount of anesthetic, and the organs such as the heart, liver and kidneys were immediately taken out and observed. There was no obvious abnormality in the organs, the colors of the organs were normal, and no bleeding and necrosis occurred. There were no significant abnormalities in the heart sections of the rats at each time period when compared to the normal rats. The cardiomyocytes were normal. No edema, no hypertrophy, no necrosis or degeneration occurred and no vacuoles or granules were formed in the cytoplasm. There were no fibrosis of the interstitial spaces of the myocardium and no inflammatory cell infiltration. FIG. 17 shows liver H&E staining. For each time period, the morphology of the liver cells was normal, no granules or vacuoles were formed, the cytoplasm was uniform, and the hepatic lobules were clear and regular. The interstitial spaces show no hemorrhagic exudation, no inflammatory cell infiltration, no fibrosis, no hepatocyte necrosis, etc. When comparing the rats' kidney section, the glomeruli had normal shapes in each time period, no glassy changes and sclerosis, no thickening of the glomerular basement membrane, no inflammatory cell infiltration and necrosis. The epithelial cells had a clear structure, no deformation or congestion, no granules or vacuoles, no degeneration and necrosis.

According to the H&E pathological staining of the important organs for the various time periods, there were no obvious abnormalities in the heart, liver and kidney of the SD rats. This indicates that the bone cement products are fairly biocompatible with tissue.

16. Bone cement product injected into subchondral tibia bone of guinea pigs

A bone cement injection test was conducted on the subchondral tibia bone of guinea pigs. First, the guinea pigs were temporarily anesthetized with diethyl ether. The guinea pigs were weighed and then anesthetized with 10% of chloral hydrate according to their weight. After the guinea pigs were completely comatose, the guinea pig hairs were removed, partially disinfected with iodine, and the iodine solution was wiped off with rubbing alcohol. An incision was made along the inside of the humerus to open the joint capsule of the knee, exposing the cartilage. The subchondral tibia bone was drilled with a 1 mm drill bit to a 5 mm depth. Pre-sterilized bone cement product 2 or PMMA bone cement is mixed and injected into the drill holes, and carefully sealed with bone wax. The remaining blood on the body was cleaned. The guinea pigs were kept in separate cages to prevent the guinea pigs from biting each other and to simulate a natural experimental environment. After 2 months, the guinea pigs were euthanized and their left tibia was harvested and stored in 10% formalin.

As shown in FIG. 18, Bruker Sky Scan 1076 Micro-CT machine, with the three-dimensional pixel setting was 18 mm, voltage at 100 kV, exposure time at 2356 ms, 2 frames per second, aluminum beam filter thickness at 1 mm, was used to scan the guinea pigs' left tibia bone. A 3D model of the tibia bone was reconstructed by the software.

As shown in FIG. 19, the three-dimensional reconstruction showed significant new bone formation on the bone cement product 2, showing better osteogenic ability than the PMMA bone cement. In addition, the subchondral bone cyst area was selected as a region of interest (ROI). The osteogenesis (BV/TV, %) and trabecular bone separation (tb.sp, mm) were analyzed.

As shown in Table 5, bone cement product 2 shows a higher osteogenesis volume and lower trabecular bone separation than PMMA cement.

TABLE 5

| # | Sample | Osteogenesis (%) | Trabecular bone separation (mm) |
|---|---|---|---|
| 1 | PMMA | 7.6 | 38.5 |
| 2 | Bone Cement Product 2 | 12.5 | 34.3 |

Hard Tissue Sectioning and Histological Staining

The left tibia sample of the guinea pig was excised and the excess tissue was trimmed until only the knee joint remained.

Dehydration: The hard tissue was sequentially soaked with 50%, 70%, 90%, 100% ethanol and then cleared with toluene and methyl methacrylate.

Waxing and Slicing: A mixture of methyl methacrylate, benzoyl peroxide and dimethyl p-methylaniline was used to embed and stored in the dark at 4° C. until the polymer block hardened. The tissue block was sectioned into pieces 40 μm to 70 μm thick with a microtome.

Giemsa Staining

The sections was stirred gently in 1% formic acid for 30 seconds, then exposed and quickly rinsed with water and stained in Giesma stain solution at 4° C. for 10 minutes. The excess staining solution was quickly rinsed off in water and the sections were air dried.

Microscopy: A tissue section was prepared and photographed using an Eclipse TE 2000, a fluorescent/phase contrast microscope.

As shown in FIG. 20, the bone cell layer was observed on the surface of bone cement product 2, and the fibrous layer was observed on the PMMA bone cement surface. In contrast, bone cement product 2 exhibits better biocompatibility and osteoconductivity, resulting in better new bone materials interface and providing better mechanical support for subchondral bone cysts.

All documents mentioned in this application are hereby incorporated by reference just as each document is cited separately as a reference. In addition, it is to be understood that various modifications and changes may be made by those skilled in the art after reading the above teachings of the present invention. These equivalent forms also fall within the scope defined by the claims appended hereto.

The invention claimed is:

1. Bone material composite granules comprising a copolymer of hydroxyethyl methacrylate (HEMA) and methyl methacrylate (MMA); and calcium phosphate coating on the surface of the copolymer,
   wherein the mole ratio of HEMA to MMA is 1:4-1:12,
   wherein the copolymer has an average diameter $d_1$ in the range of 300 to 600 nm,
   wherein the bone material composite granules have an average diameter $d_2$ of 400 to 750 nm,
   wherein the distribution ratio of the bone material composite granules in the size range of 400-750 nm is ≥95%, and
   wherein the setting time of the bone material composite granules ranges from 10-15 min.

2. The bone material composite granules of claim 1, wherein
   the $d_2$:$d_1$ ratio has a range of 1.1-1.8.

3. A method for preparing the bone material composite granules according to claim 1, comprising the steps:
   1) providing a copolymer of hydroxy(ethyl) methacrylate (HEMA) and methyl methacrylate (MMA), wherein the molar ratio of the hydroxy(ethyl) methacrylate to methyl methacrylate is 1:4-1:12;
   2) reacting the copolymer with $Ca(OH)_2$ and $H_3PO_4$ to obtain a copolymer with a surface coated with calcium phosphate; thereby producing the composite granules; and
   3) optionally, drying the composite granules.

4. A bone cement product comprising:
   (1) component A, comprising the bone material composite granules of claim 1; and (2) component B, comprising methyl methacrylate and an accelerator, the accelerator is selected from the group consisting of: dimethyl-p-toluidine (DMPT), methyl ethyl ketone peroxide (MEKP), dicumyl peroxide, perester, decanoyl peroxide, tert-butane, tert-pentane, azobisisobutyronitrile (AIBN), caproic acid, and combination thereof.

5. The bone cement product according to claim 4, wherein said component A further comprises a catalyst and a contrast agent.

6. The bone cement product according to claim 5, wherein said catalyst is selected from the group consisting of: benzoyl peroxide, N,N-dimethylamirio-4-benzyl laurate, N,N-dimethylamino-4-benzyl oleate, and combination thereof.

7. The bone cement product according to claim 4, wherein in said component B, the volume ratio of said methyl methacrylate to the accelerator is 10:1-150:1.

8. An in vitro method for non-therapeutic preparation of a bone graft, comprising the steps:
(a) providing the bone material composite granules of claim 1;
(h) mixing the bone material composite granules with a setting liquid to form a mixture; and
(c) setting the mixture to form the bone graft,
wherein the bone graft has (i) a bending strength ≥50 MPa, and (ii) a compressive strength ≥100 MPa.

9. A method of manufacturing a bone filler for the treatment of a bone disease comprising including the bone material composite granules of claim 1.

10. The method of claim 9, wherein said bone disease is selected from the group consisting of: osteonecrosis, osteoporosis, osteoarthritis, vertebroplasty, bone fracture, bone cyst, alveolar bone atrophy, subchondral bone defect, subchondral bone cyst, maxillofacial surgery, plastic surgery, and minimally invasive bone surgery.

11. A method of manufacturing a bone filler for the treatment of a bone disease comprising including the bone cement product of claim 4.

12. The method of claim 11, wherein said bone disease is selected from the group consisting of: osteonecrosis, osteoporosis, osteoarthritis, vertebroplasty, bone fracture, bone cyst, alveolar bone atrophy, subchondral bone defect, subchondral bone cyst, maxillofacial surgery, plastic surgery, and minimally invasive bone surgery.

13. The bone material composite granules of claim 1, wherein the mole ratio of HEMA to MMA is 1:5-1:10.

14. The method of claim 3, wherein the mole ratio of HEMA to MMA is 1:5-1:10.

* * * * *